(12) United States Patent
Penichet et al.

(10) Patent No.: US 8,734,799 B2
(45) Date of Patent: May 27, 2014

(54) UNCONJUGATED ANTI-TFR ANTIBODIES AND COMPOSITIONS THEREOF FOR THE TREATMENT OF CANCER

(75) Inventors: Manuel L. Penichet, Los Angeles, CA (US); Tracy R. Wells, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/639,172

(22) PCT Filed: Apr. 11, 2011

(86) PCT No.: PCT/US2011/031934
§ 371 (c)(1),
(2), (4) Date: Oct. 3, 2012

(87) PCT Pub. No.: WO2011/130164
PCT Pub. Date: Oct. 20, 2011

(65) Prior Publication Data
US 2013/0028891 A1 Jan. 31, 2013

Related U.S. Application Data

(60) Provisional application No. 61/323,740, filed on Apr. 13, 2010.

(51) Int. Cl.
*A61K 38/00* (2006.01)
(52) U.S. Cl.
USPC ............... 424/143.1; 424/133.1; 424/155.1; 424/142.1
(58) Field of Classification Search
None
See application file for complete search history.

(56) References Cited

U.S. PATENT DOCUMENTS

| | | | |
|---|---|---|---|
| 5,667,781 A * | 9/1997 | Trowbridge et al. | 424/143.1 |
| 6,329,508 B1 | 12/2001 | Friden | |
| 2006/0029597 A1* | 2/2006 | Chintalacharuvu et al. | 424/133.1 |
| 2006/0286030 A1 | 12/2006 | Boumsell | |

OTHER PUBLICATIONS

Trowbridge et al (Nature, 1981, 294:171-173).*
Ng et al (Blood, 2006, 108:2745-2754).*
Chuntharapai et al (Journal of Immunology, 2001, 166:4891-4898).*
International Search Report received in PCT/US2011/031934, mailed Dec. 26, 2011.
Lesley, J. et al. (1985) "Inhibition of Cell Growth by Monoclonal Anti-Transferrin Receptor Antibodies" Molecular and Cellular Biology, 5(8):1814-1821.
Ng, P. et al. (2002) "An Anti-Transferrin Receptor-Avidin Fusion Protein Exhibits Both Strong Proapoptotic Activity and the Ability to Deliver Various Molecules into Cancer Cells" PNAS, 99(16): 10706-10711.
Moura, I. et al. (2004) "A Neutralizing Monoclonal Antibody (mAb A24) Directed Against the Transferrin Receptor Induces Apoptosis of Tumor T Lymphocytes from ATL Patients" Blood, 103(5):1838-1845.
Lepelletier, Y. et al. (2007) "Prevention of Mantle Lymphoma Tumor Establishment by Routing Transferrin Receptor Toward Lysosomal Compartments" Cancer Res. 67(3): 1145-1154.
Trowbridge, I. et al (1981) "Anti-Transferrin Receptor Monoclonal Antibody and Toxin-Antibody Conjugates Affect Growth of Human Tumour Cells" Nature, 294:171-173.
Daniels, T. et al. (2006) "The Transferrin Receptor Part I: Biology and Targeting with Cytotoxic Antibodies for the Treatment of Cancer" Clinical Immunology, 121:144-158.
Schnyder, A. et al. (2005) "In vitro and in vivo Drug Targeting Using Biotinylated Immunoliposomes", Universitat Basel.
Walus, L. et al. (1996) "Enhanced Uptake of rsCD4 Across the Rodent and Primate Blood-Brain Barrier After Conjugation to Anti-Transferrin Receptor Antibodies" Journal of Pharmacology and Experimental Therapeutics, 277:1067-1075.
Ng, P. et al. (2005) "Molecular Events Contributing to Cell Death in Malignant Human Hematopoietic Cells Elicited by an IgG3-avidin Fusion Protein Targeting the Transferrin Receptor" Blood, 108(8):2745-2754.
White, S. et al. (1990) "Combinations of Anti-Transferrin Receptor Monoclonal Antibodies Inhibit Human Tumor Cell Growth in Vitro and in Vivo: Evidence Synergistic Antiproliferative Effects" Cancer Research, 50:6295-6301.
Brooks, D. et al. (1995) "Phase Ia Trial of Murine Immunoglobulin A Antitransferrin Receptor Antibody 42/6" Clinical Cancer Research, 1: 1259-1265.
Rodriguez, J. et al. (2007) "Binding Specificity and Internalization Properties of an Antibody-Avidin Fusion Targeting the Human Transferrin Receptor" Journal of Controlled Release, 124:35-42.
International Preliminary Report on Patentability and Written Opinion from the International Searching Authority received in PCT/US2011/031934, issued Oct. 16, 2012.

* cited by examiner

*Primary Examiner* — Misook Yu
*Assistant Examiner* — Julie Wu
(74) *Attorney, Agent, or Firm* — Suzannah K. Sundby, Esq.; Smith, Gambrell & Russell, LLP

(57) ABSTRACT

Disclosed herein are methods and compositions for treating cancer. In particular, the in vivo efficacy of unconjugated anti-TfR antibodies, such as ch128.1, are disclosed herein.

13 Claims, 2 Drawing Sheets

UNCONJUGATED ANTI-TFR ANTIBODIES AND COMPOSITIONS THEREOF FOR THE TREATMENT OF CANCER

CROSS-REFERENCE TO RELATED APPLICATIONS

This application claims the benefit of U.S. Patent Application Ser. No. 61/323,740, filed 13 Apr. 2010, which is herein incorporated by reference in its entirety.

ACKNOWLEDGEMENT OF GOVERNMENT SUPPORT

This invention was made with Government support of Grant Nos. CA107023, CA138559, and CA009120, awarded by the National Institutes of Health. The Government has certain rights in this invention.

BACKGROUND OF THE INVENTION

1. Field of the Invention

The present invention generally relates to anti-transferrin receptor antibodies and their use in the treatment of cancer.

2. Description of the Related Art

Multiple myeloma is a clonal B-cell malignancy that accounts for 10-15% of hematopoietic malignancies and 2% of all cancer deaths in the United States. See Jemal et al. (2010) CA Cancer J Clin 60(5):277-300. Within the past decade the overall survival rate of multiple myeloma has increased dramatically due to the utilization of thalidomide and its derivative lenalidomide, as well as the proteosome inhibitor bortezomib. See Laubach et al. (2010) Med Oncol 27(Suppl 1):S1-S6. Combination therapies of these new drugs with dexamethasone, prednisone, melphalan, or anthracyclines (with or without autologous stem cell transplantation) have improved survival of multiple myeloma patients. See Palumbo et al. (2009) Leukemia 23(3):449-56. However, multiple myeloma remains incurable and novel therapies are still needed. Additionally, there are no FDA-approved antibody-based therapies for the treatment of multiple myeloma. A successful antibody-based therapy for other B-cell malignancies is rituximab (Rituxan®), a chimeric IgG1 that targets CD20. See Bello & Sotomayor (2007) Hematology Am Soc Hematol Educ Program 233-242. This antibody alone or combined with various forms of chemotherapy is FDA approved for the treatment of B-cell malignancies including chronic lymphocytic leukemia (CLL) and non-Hodgkin's lymphoma (NHL). Due to the small percentage of multiple myeloma that are CD20$^+$ (13-22%), rituximab is not a common treatment for multiple myeloma. Additionally, only 10% of CD20$^+$ multiple myeloma patients have shown a partial response to rituximab treatment. See Kapoor et al. (2008) Br J Haematol 141(2):135-148. In lymphoma patients where rituximab has significantly increased survival, resistance to treatment continues to be a problem. See Oflazoglu & Audoly (2010) mAbs 2(1):14-19. Therefore, there is still a need for the development of new therapies for the treatment of B-cell malignancies as a whole, and for multiple myeloma in particular.

SUMMARY OF THE INVENTION

The present invention is directed to unconjugated anti-TfR antibodies for treating B-cell malignancies, such as multiple myeloma, in subjects.

In some embodiments, the present invention provides a method for treating a cancer in a subject or reducing the risk of the cancer in the subject which comprises administering to the subject at least one unconjugated anti-TfR antibody as the sole or primary therapeutic agent. The unconjugated anti-TfR antibody is reactive with at least a portion of a human transferrin receptor, such as transferrin receptor protein 1 (TfR1). In some embodiments, the unconjugated anti-TfR antibody is a human antibody, chimeric human antibody (i.e. part human origin), or a humanized antibody. In some embodiments, the isotype of the unconjugated anti-TfR antibody is IgA, IgD, IgE, IgG or IgM, preferably IgG1 or IgG3. In some embodiments, the unconjugated anti-TfR antibody comprises light and heavy chain variable regions of murine monoclonal 128.1, human kappa light chain, and human gamma 3 heavy chain, and the unconjugated anti-TfR antibody is specific for human transferrin receptor protein 1 (TfR1). In some embodiments, the unconjugated anti-TfR antibody is ch128.1 or 128.1. In some embodiments, the unconjugated anti-TfR antibody is administered in a therapeutically effective amount. In some embodiments, the unconjugated anti-TfR antibody is administered in the form of a pharmaceutical composition which comprises a pharmaceutically acceptable excipient. In some embodiments, a secondary therapeutic agent is administered to the subject before, during, or after administration of the unconjugated anti-TfR antibody. In some embodiments, the pharmaceutical composition which is administered to the subject further comprises a secondary therapeutic agent. In some embodiments, a prophylactically effective amount or a therapeutically effective amount of the unconjugated anti-TfR antibody is administered as a single dose or as multiple doses.

In some embodiments, the present invention provides a use of an unconjugated anti-TfR antibody as described herein for the manufacture of a medicament for treating cancer such as a B-cell malignancy. Preferably, the unconjugated anti-TfR antibody is the sole or primary therapeutic agent in the medicament. The unconjugated anti-TfR antibody is reactive with at least a portion of a human transferrin receptor, such as transferrin receptor protein 1 (TfR1). In some embodiments, the unconjugated anti-TfR antibody is a human antibody, chimeric human antibody, or a humanized antibody. In some embodiments, the isotype of the unconjugated anti-TfR antibody is IgA, IgD, IgE, IgG or IgM, preferably IgG1 or IgG3. In some embodiments, the unconjugated anti-TfR antibody comprises light and heavy chain variable regions of murine monoclonal 128.1, human kappa light chain, and human gamma 3 heavy chain, and the unconjugated anti-TfR antibody is specific for human transferrin receptor protein 1 (TfR1). In some embodiments, the unconjugated anti-TfR antibody is ch128.1 or 128.1. In some embodiments, the unconjugated anti-TfR antibody is administered in a therapeutically effective amount. In some embodiments, the unconjugated anti-TfR antibody is administered in the form of a pharmaceutical composition which comprises a pharmaceutically acceptable excipient. In some embodiments, a secondary therapeutic agent is administered to the subject before, during, or after administration of the unconjugated anti-TfR antibody. In some embodiments, the pharmaceutical composition which is administered to the subject further comprises a secondary therapeutic agent. In some embodiments, a prophylactically effective amount or a therapeutically effective amount of the unconjugated anti-TfR antibody is administered as a single dose or as multiple doses.

In some embodiments, the present invention provides a use of an unconjugated anti-TfR antibody as described herein for the manufacture of a medicament for treating cancer such as a B-cell malignancy, wherein the medicament is prepared to be administered as a single dose or as several doses. Preferably, the unconjugated anti-TfR antibody is the sole or primary therapeutic agent in the medicament. The unconjugated anti-TfR antibody is reactive with at least a portion of a human transferrin receptor, such as transferrin receptor protein 1 (TfR1). In some embodiments, the unconjugated anti-TfR antibody is a human antibody, chimeric human antibody, or a humanized antibody. In some embodiments, the isotype of the unconjugated anti-TfR antibody is IgA, IgD, IgE, IgG or IgM, preferably IgG1 or IgG3. In some embodiments, the unconjugated anti-TfR antibody comprises light and heavy chain variable regions of murine monoclonal 128.1, human kappa light chain, and human gamma 3 heavy chain, and the unconjugated anti-TfR antibody is specific for human transferrin receptor protein 1 (TfR1). In some embodiments, the unconjugated anti-TfR antibody is ch128.1 or 128.1. In some embodiments, the unconjugated anti-TfR antibody is administered in a therapeutically effective amount. In some embodiments, the unconjugated anti-TfR antibody is administered in the form of a pharmaceutical composition which comprises a pharmaceutically acceptable excipient. In some embodiments, a secondary therapeutic agent is administered to the subject before, during, or after administration of the unconjugated anti-TfR antibody. In some embodiments, the pharmaceutical composition which is administered to the subject further comprises a secondary therapeutic agent. In some embodiments, a prophylactically effective amount or a therapeutically effective amount of the unconjugated anti-TfR antibody is administered as a single dose or as multiple doses.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein.

DETAILED DESCRIPTION OF THE INVENTION

Figure 1A:
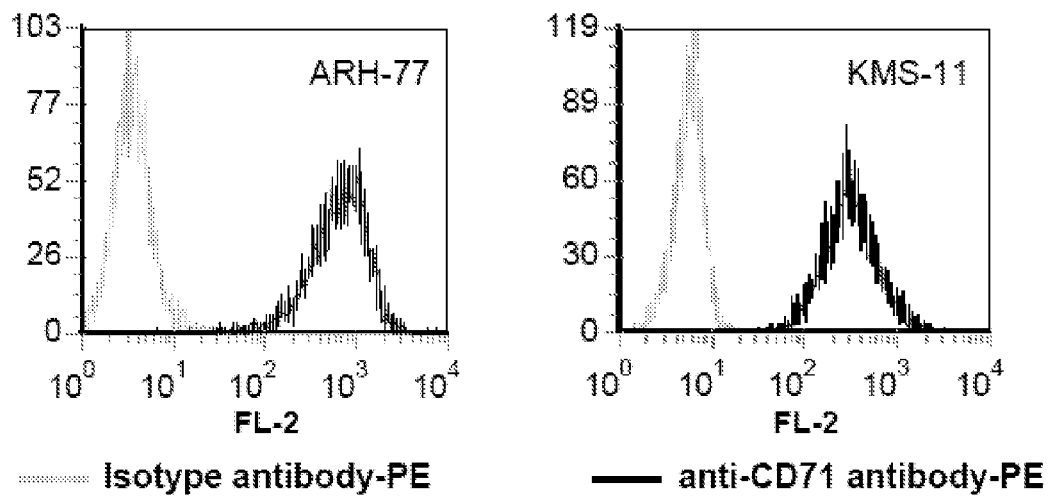
FIG. 1A are graphs showing the cell surface expression of TfR1 (CD71) on the surface of KMS-11 and ARH-77 cells as determined by flow cytometry. Cells were labeled with either an isotype-PE conjugated control antibody (gray line) or anti-CD71-PE conjugated antibody (black line).

TfR1 (CD71) expression is increased on a wide variety of cancer cells, including hematopoietic cancers and in some cases, such as chronic lymphocytic leukemia (CLL) and non-Hodgkin's lymphoma (NHL), its expression can be correlated with tumor stage or prognosis. See Daniels et al. (2006) Clin Immunol 121(2):144-158, which is herein incorporated by reference. Due to its increased expression on cancer cells, its extracellular accessibility, its central role in cancer pathology, and its ability to internalize, the TfR1 has been used extensively as a target for cancer therapy. See Daniels et al. (2006) Clin Immunol 121(2):144-158 and Daniels et al. (2006) Clin Immunol 121(2):159-176, which are herein incorporated by reference. In fact, a recent study showed that transferrin-targeted nanoparticles carrying a small interfering RNA (siRNA) could be systemically delivered to patients with solid tumors resulting in specific gene inhibition within cancer biopsies. See Davis et al. (2010) Nature 464(7291):1067-1070.

In order to target human cancer cells that overexpress the TfR1, an antibody fusion protein that consists of a mouse/human chimeric IgG3 specific for the TfR1 with avidin genetically fused to the $C_H3$ domains of the antibody (ch128.1Av; previously known as anti-human TfR IgG3-Av) was developed. See Ng et al. (2002) PNAS USA 99(16):10706-10711. This fusion protein was originally designed as a universal delivery system that could be used to carry biotinylated molecules into cancer cells.

ch128.1Av was shown to exhibit direct cytotoxicity (antiproliferative and/or pro-apoptotic activity) against cancer cells in vitro, while the antibody itself, i.e. ch128.1 (or its parental murine monoclonal antibody 128.1), exhibited low to no direct cytotoxic activity in vitro compared to the antibody-avidin fusion protein. See e.g. Ng et al. (2002); Ng et al. (2006) Blood 108 (8):2745-2754; and U.S. 20030133938, which are herein incorporated by reference, see also FIG. 1B. Thus, it was believed that ch128.1 itself or its parental murine monoclonal antibody 128.1, would not exhibit significant direct cytotoxic activity in vivo, which would decrease its therapeutic utility (if any) in the treatment of cancer especially in cancer cells that show no in vitro sensitivity to this antibody. In fact, the in vitro cytotoxicity of anti-TfR antibodies has been used as a fact that indicates whether or not an anti-TfR antibody is worthy to move into in vivo studies. See White et al. (1990) Cancer Res 50(19):6295-6301, which is herein incorporated by reference. Therefore, ch128.1 was used as a control in subsequent in vivo activity assays of the antibody-avidin fusion protein.

Unexpectedly, it was found that ch128.1 exhibits remarkable anti-cancer activity in vivo against human xenograft models of multiple myeloma in SCID-Beige mice. In fact, it was found that the activity of ch128.1 is significantly better than that exhibited by the antibody-avidin fusion protein. These results, which are disclosed herein, are surprising since ch128.1 itself exhibited limited or no in vitro cytotoxic activity against hematological malignant cells, such as myeloma, leukemia, and lymphoma cells. Therefore, the present invention provides methods of treating cancer in a subject which comprises, consists essentially of, or consists of administering to the subject at least one unconjugated anti-transferrin receptor antibody as the sole or primary therapeutic agent. The present invention also provides compositions for treating cancer which comprise, consist essentially of, or consist of at least one unconjugated anti-transferrin receptor antibody as the sole or primary therapeutic agent.

As used herein, an "antibody" refers to a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin, e.g. antibody, structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively. As used herein, an "antibody" can be an intact immunoglobulin or a well characterized fragment thereof which may be produced by digestion with various peptidases or recombinant techniques known in the art. See Fundamental Immunology, W. E. Paul, ed., Raven Press, New York (1999). The term "antibody" also includes single chain antibodies, e.g. single chain Fv (sFv or scFv) antibodies in which a variable heavy and a variable light chain are joined together (directly or through a peptide linker) to form a continuous polypeptide. In some embodiments, the antibody is a synthetic antibody, e.g. one or more antibody fragments such as Fc fragments and/or scFv fragments chemically conjugated or genetically fused together.

As used herein, an "unconjugated antibody" refers to an antibody which is not fused or linked (covalently or non-covalently) to another molecule. As used herein, usage of the phrase the "sole or primary therapeutic agent" means that the unconjugated antibody is itself the active therapeutic agent, i.e. the unconjugated antibody is not employed as a drug delivery carrier or targeting molecule that is used to deliver or target a given compound or composition. In embodiments where the unconjugated antibody is administered as the primary therapeutic agent, one or more secondary therapeutic agents may be administered to the subject before, during or after administration of the unconjugated antibody. In embodiments where a secondary therapeutic agent is administered during administration of the unconjugated antibody, the secondary therapeutic agent and the unconjugated antibody may be administered in the form of one composition or separate compositions.

As used herein, an "anti-transferrin receptor (anti-TfR) antibody" refers to an antibody which is reactive, i.e. reacts or cross-reacts, with at least a portion of a human transferrin receptor, preferably a human transferrin receptor protein 1 (TfR1, also known as CD71), e.g. Accession No. NP 003225, which is herein incorporated by reference. In some embodiments, the anti-TfR antibody is a mouse, rat or human antibody. In some embodiments, the anti-TfR antibody is a chimeric antibody such as a mouse-human chimeric antibody or a humanized antibody. As used herein, a "human chimeric antibody" is one which has some human antibody sequences. In some embodiments, the isotype of the anti-TfR antibody is IgA, IgD, IgE, IgG or IgM. In some embodiments, the anti-TfR antibody is an IgG1 or an IgG3 antibody. In some embodiments, the anti-TfR antibody is one of the unconjugated antibodies described in U.S. Pat. No. 6,329,508; and Ng et al. (2006) Blood 121(2):144-158, which are herein incorporated by reference. In some embodiments, the unconjugated anti-TfR antibody is ch128.1. In some embodiments, the unconjugated anti-TfR antibody is specific for the same epitope that ch128.1 is specific for, i.e. specifically recognizes. It should be noted that the sequences of ch128.1, as used herein, are those as set forth in Tables 5 and 6 of U.S. Pat. No. 6,329,508 (which is herein incorporated by reference in its entirety) with the following amino acid substitutions in the light chain variable region: R31D, R39K, P40S, N53K, and A80K.

In some embodiments, the anti-TfR antibody according to the present invention is specific for a human transferrin receptor protein 1 (TfR1), e.g. Accession No. NP 003225. As used herein, an antibody that is "specific for" a given molecule refers to the character of the antibody which recognizes and interacts with a given molecule, e.g. a transferrin receptor, but does not substantially recognize and interact with other molecules in a sample under given conditions.

Monoclonal antibodies and fragments thereof, e.g. scFv, reactive with at least a portion of the transferrin receptor can be obtained (e.g. OX-26, B3/25 (Omary et al. (1980) Nature 286:888-891), T56/14 (Gatter et al. (1983) J Clin Path 36:539-545; Jefferies et al. (1985) Immunology 54:333-341), OKT-9 (Sutherland et al. (1981) PNAS USA 78:4515-4519), L5.1 (Rovera, C. (1982) Blood 59:671-678), 5E-9 (Haynes et al. (1981) J Immunol 127:347-351), RI7 217 (Trowbridge et al. (1981) PNAS USA 78:3039 and T58/30 (Omary et al. cited supra) using methods known in the art. See e.g. Crépin et al. (2010) Cancer Res 70:5497-5506, which is herein incorporated by reference. A crude or purified protein or peptide comprising at least a portion of the transferrin receptor can be used as the immunogen. An animal is vaccinated with the immunogen to obtain an anti-transferrin receptor antibody-producing spleen cells. The species of animal immunized will vary depending on the species of monoclonal antibody desired. The antibody producing cell is fused with an immortalizing cell (e.g. myeloma cell) to create a hybridoma capable of secreting anti-transferrin receptor antibodies. The unfused residual antibody-producing cells and immortalizing cells are eliminated. Hybridomas producing the anti-transferrin receptor antibodies are selected using conventional techniques and the selected anti-tranferrin receptor antibody producing hybridomas are cloned and cultured. See e.g.

Helguera et al. "Monoclonal Antibodies, Human, Engineered" in ENCYCLOPEDIA OF INDUSTRIAL BIOTECHNOLOGY: BIOSEPARATION, AND CELL TECHNOLOGY, ed. Michael C. Flickinger (2010) John Wiley & Sons, Inc., which is herein incorporated by reference.

Polyclonal antibodies can be prepared by immunizing an animal with a crude or purified protein or peptide comprising at least a portion of a transferrin receptor. The animal is maintained under conditions whereby antibodies reactive with a transferrin receptor are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g. IgD, IgE, IgM, and IgA).

As used herein, a "subject" refers to a mammal, preferably a human who may be a patient, e.g. under the care of a physician.

As used herein, the term "pharmaceutical composition" refers to a composition suitable for pharmaceutical use in a subject. A pharmaceutical composition generally comprises an effective amount of an active agent, e.g. an unconjugated anti-TfR antibody according to the present invention, and a pharmaceutically acceptable carrier, e.g. a buffer, adjuvant, and the like.

As used herein an "effective amount" refers to a dosage or amount sufficient to produce a desired result. The desired result may comprise an objective or subjective improvement in the recipient of the dosage or amount, e.g. long-term survival, decrease in number and/or size of tumors, effective prevention of a disease state, and the like.

The unconjugated anti-TfR antibodies and compositions thereof may be used in prophylactic treatments and/or therapeutic treatments.

A "prophylactic treatment" is a treatment administered to a subject who does not display signs or symptoms of a disease, pathology, or medical disorder, or displays only early signs or symptoms of a disease, pathology, or disorder, such that treatment is administered for the purpose of diminishing, preventing, or decreasing the risk of developing the disease, pathology, or medical disorder. A prophylactic treatment functions as a preventative treatment against a disease or disorder. A "prophylactic activity" is an activity of an agent, such as an unconjugated anti-TfR antibody or composition thereof, which when administered to a subject who does not display signs or symptoms of a pathology, disease or disorder (or who displays only early signs or symptoms of a pathology, disease, or disorder) reduces or prevents the risk of the subject developing the pathology, disease, or disorder. A "prophylactically effective amount" of one or more an unconjugated anti-TfR antibodies, refers to an amount that reduces or prevents the development of a pathology, disease or disorder as compared to a control.

A "therapeutic treatment" is a treatment administered to a subject who displays symptoms or signs of pathology, disease, or disorder, in which treatment is administered to the subject for the purpose of diminishing or eliminating those signs or symptoms of pathology, disease, or disorder. A "therapeutic activity" is an activity of an agent, such as an unconjugated anti-TfR antibody or composition thereof, which reduces, eliminates, or treats signs or symptoms of a pathology, disease or disorder, when administered to a subject suffering from such signs or symptoms. A "therapeutically effective amount" of one or more unconjugated anti-TfR antibodies, refers to an amount that uses, eliminates, or treats signs or symptoms of the pathology, disease or disorder as compared to control.

In some embodiments, one or more unconjugated anti-TfR antibodies may be administered to a subject who has been treated for cancer, e.g. surgery to remove cancerous tissue/cells, and/or who is in remission.

In some embodiments, one or more unconjugated anti-TfR antibodies may be used in prophylactic treatments. For example, a subject at risk of developing a cancer such as multiple myeloma or other B-cell maligancies may be administered a prophylactically useful amount of one or more unconjugated anti-TfR antibodies according to the present invention. In some embodiments, one or more unconjugated anti-TfR antibodies may be used in therapeutic treatments. For example, a subject who has been diagnosed as having a cancer such as multiple myeloma may be administered a therapeutically useful amount one or more unconjugated anti-TfR antibodies according to the present invention.

In some embodiments, an unconjugated anti-TfR antibody is administered in combination with one or more known therapeutic compounds and/or strategies, such as rituximab (RITUXAN®, Genentech, San Francisco, Calif.). In some embodiments, an unconjugated anti-TfR antibody is administered in place of one or more known therapeutic compounds and/or strategies. In some embodiments, different unconjugated anti-TfR antibodies can be used in conjunction with each other. For example, in some treatment regimens different unconjugated anti-TfR antibodies can be administered to a subject in the same course of treatment.

In some embodiments, the cancer is one that expresses high levels of transferrin receptor 1 (CD71), such as malignant brain tumors, breast cancer, bladder cancer, gliomas, lung cancer, chronic lymphocytic leukemia, non-Hodgkin's lymphoma, colorectal cancer, and hematopoietic malignancies. In some embodiments, the cancer is multiple (disseminated) myeloma, lymphoma, aggressive lymphoma, an epithelial tumor, a metastatic epithelial tumor, a mesenchymal tumor, leukemia, or the like. One skilled in the art may readily determine which cancers express the transferrin receptor using methods known in the art such as immunohistochemistry and flow cytometry. For example, flow cytometry may be used to detect CD71 surface expression in single cell suspensions, e.g. cells of interest are incubated for 30 minutes on ice with either phycoerythrin (PE)-conjugated mouse IgG2a isotype control or PE-conjugated mouse anti-human CD71 (hTfR1) monoclonal antibodies (both from BD Biosciences). After staining, all cells were washed, fixed, and analyzed by flow cytometry.

In the experiments below, the following cell lines and antibodies were used.

Human Cell Lines

ARH-77 (EBV-transformed lymphoblastoid cells, ATCC # CRL-1621) was purchased from ATCC (American Type Culture Collection, Manassas, Va.) and cultured in RPMI 1640 (Invitrogen Corporation, Carlsbad, Calif.). KMS-11 human myeloma cells were a kind gift from Lawrence Boise (Emory University, Namba et al. (1989) In vitro Cell Dev Biol. 25(8): 723-729) and were cultured in IMDM (Invitrogen). All cell lines were grown in media supplemented with 100 U/mL penicillin, 10 µg/mL streptomycin, and 10% (v/v) heat inactivated fetal bovine serum (FBS; Atlanta Biologicals, Atlanta, Ga.) in 5% $CO_2$ at 37° C.

Antibodies and Antibody Fusion Proteins ch128.1 and ch128.1Av have been described previously. See Ng (2002) and Ng (2006), which are herein incorporated by reference. ch128.1 and ch128.1Av contain the variable regions of the murine monoclonal anti-human TfR IgG1 antibody 128.1. See White et al. (1990) Cancer Res 50(19):6295-6301, which is herein incorporated by reference. ch128.1 and ch128.1Av, and their isotype negative controls, contain kappa (κ) light chains, were expressed in murine myeloma cells, and were purified from cell culture supernatants as described previously. See Helguera & Penichet (2005) Methods Mol Med 109:347-374, which is herein incorporated by reference.

In Vitro Efficacy

Previously, various conjugated (antibody-avidin fusion protein) and unconjugated anti-TfR antibodies were assayed for their in vitro cytotoxicity. In these experiments, the conjugated forms exhibited in vitro activity while the unconjugated forms exhibited little, if any, activity in vitro. In particular, the original monoclonal 128.1 did not exhibit anti-proliferative activity against the human erythroleukemia cell line K562. See Ng et al. (2002) PNAS USA 99(16):10706-10711, which is herein incorporated by reference. In highly sensitive cells, unconjugated the mouse/human chimeric version anti-TfR IgG3 (ch128.1) exhibited an anti-proliferative/pro-apoptotic activity against hematological cancer cells such as ARH-77 cells, which activity was significantly lower than that of the corresponding avidin fusion protein, i.e. ch128.1Av. If fact, even using 3-fold higher concentration of the antibody without avidin (ch128.1) in highly sensitive cells such as ARH-77 it is not possible to observe the same level of pro-apoptotic cytotoxic effect as shown by use of our antibody-avidin fusion protein ch128.1Av. See Ng et al. (2006) Blood 108(8):2745-2754, which is herein incorporated by reference.

Figure 1B:
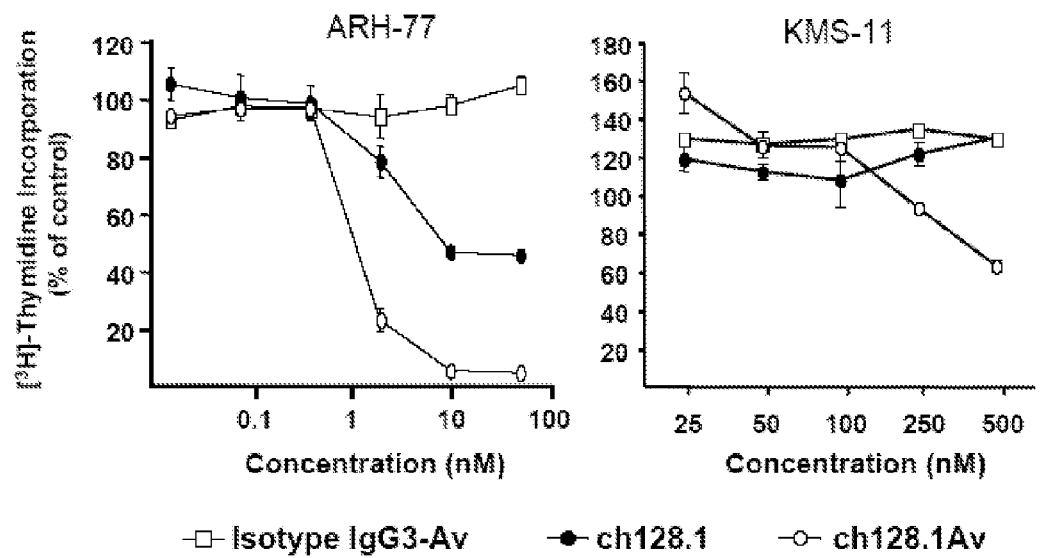
FIG. 1B are graphs which show the in vitro cytotoxicity of ch128.1 and ch128.1Av against KMS-11 and ARH-77 cells. Cells were treated with various concentrations (ranging from 25-500 nM for KMS-11 cells and 0.016-50 nM for ARH-77 cells) of ch128.1, ch128.1Av, or the isotype IgG3-Av (isotype control of ch128.1Av) for a total of 96 hours. Cytotoxicity was measured using the [$^3$H]-thymidine incorporation assay known in the art. The average of triplicate wells is shown with the standard deviation. Data are presented as a percent of radioactivity incorporated into control cells and are representative of three independent experiments.

In further experiments, two different malignant B-cell lines were used. Specifically, a human B-lymphoblastoid cell line ARH-77 and a human myeloma cell line KMS-11 were used to evaluate the in vitro efficacy of ch128.1Av and ch128.1. For these experiments, cells were treated in triplicate in with various concentrations of the indicated treatments for 96 hours. Proliferation was monitored using the [$^3$H]-thymidine incorporation assay as described previously. See Daniels et al. (2007) Mol Cancer Ther 6(11):2995-3008, which is herein incorporated by reference. Once again the superior anti-proliferative activity of ch128.1Av compared to ch128.1 was confirmed. In addition, it was found that KMS-11 has low in vitro sensitivity to ch128.1Av, despite high expression levels of the TfR1 (FIGS. 1A and 1B). In fact, compared to ARH-77 cells, 500 fold more of ch128.1Av was required to observe a similar effect in KMS-11 cells in vitro (FIGS. 1A and 1B). However, ch128.1 did not exhibit any in vitro anti-proliferative effect even at high concentrations (500 nM).

In Vivo Efficacy of ch128.1Av and ch128.1

As disclosed herein, in two disseminated multiple myeloma xenograft mouse models, both ch128.1Av and ch128.1 result in significant anti-tumor activity including long-term survival. The human B-lymphoblastoid cell line ARH-77 was used as a model of multiple myeloma since its intravenous injection into SCID mice leads to the development of a disease that mimics human multiple myeloma with mice developing hypercalcemia, lytic bone lesions, and hind limb paralysis. See Gado et al. (2001) Haematologica 86(3): 227-236, which is herein incorporated by reference. The human myeloma cell line KMS-11 was used as a model of multiple myeloma since as it has been used to evaluate the in vivo efficacy of many potential therapeutics for multiple myeloma including bortezomib. See Namba et al. (1989) In Vitro Cell Dev Biol 25(8):723-729 and Stein et al. (2009) Clin Cancer Res 15(8):2808-2817, which are herein incorporated by reference. For all in vivo efficacy studies, SCID-Beige mice were challenged with a lethal dose of either ARH-77 or KMS-11 cells on day 0 and treated on day 2. C.B-17 SCID-Beige mice were obtained and housed in the Defined-Flora Mouse Facility in the Department of Radiation Oncology at UCLA. The beige mutation results in impairment of NK function and these mice (SCID-Beige) also have impaired neutrophil activity. See Roder et al (1979) J Immunol 123(5): 2168-73 and Jones-Carson et al (1995) J Infect Dis. 171(6): 1664-7, which are herein incorporated by reference. 8-12 week old female mice were exposed to 3 gray total body irradiation using a MARK-1-30 irradiator (Cs-137 source, J. L. Shepherd & Associates) on the day prior to tumor challenge. Tumor challenge consisted of intravenous injection of $5\times10^6$ ARH-77 or KMS-11 cells in Hank's Buffered Salt Solution (HBSS) via the tail vein. Mice were randomized into treatment groups and treatments were given intravenously 2 days after tumor challenge also in HBSS. Survival was based on the time from tumor challenge to the development of hind-limb paralysis, when mice were euthanized. Survival plots were generated using GraphPad Prizm (version 5). Median survival and differences in survival (Log Rank Test) were determined using the same software.

Figure 2A:
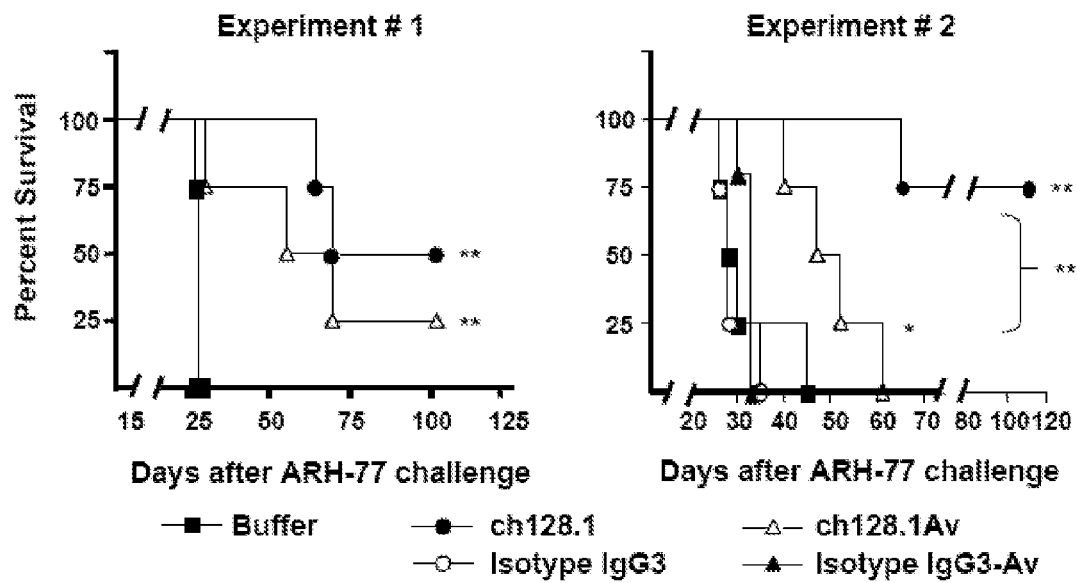
FIG. 2A are Kaplan-Meier plots showing the in vivo efficacy of ch128.1 and ch128.1Av against ARH-77. Female SCID-beige mice (8-12 weeks old) were radiated with 3 gray 24 hrs prior to the tumor challenge. The following day, mice were challenged with 5 million ARH-77 cells by intravenous injection via the tail vein. Two days later, mice were treated intravenously with buffer alone, ch128.1, or ch128.1Av (Experiment #1) or with buffer alone, ch128.1, ch128.1Av, isotype control of ch128.1 (isotype IgG3), or isotype control of ch128.1Av (isotype IgG3-Av), (Experiment #2). 100 µg of each treatment was used. Survival was recorded based on the time from tumor challenge to the development of hind-limb paralysis, when mice were euthanized. Kaplan-Meier plots were generated using GraphPad Prism (GraphPad Software, Inc., La Jolla, Calif.). * $p<0.05$, ** $p<0.01$, as determined by the Log Rank test. Animal numbers for each experiment are given in Table 1.

For each xenograft mouse model, the experiment was carried out twice. In the first experiment with ARH-77 xenographs, both ch128.1Av and ch128.1 prolonged survival compared to buffer control (FIG. 2A (Experiment #1), Table 1).

TABLE 1

Median survival of SCID-Beige mice treated with ch128.1 or ch128.1Av.

|  | ARH-77 (#1) | ARH-77 (#2) | KMS-11 (#1) | KMS-11 (#2) |
|---|---|---|---|---|
| Buffer | 28 (n = 4) | 29 (n = 4) | 33 (n = 8) | 43 (n = 4) |
| ch128.1 | 85 (n = 4) | >100 (n = 4) | >100 (n = 10) | >100 (n = 5) |
| ch128.1Av | 62 (n = 4) | 50 (n = 4) | 49 (n = 10) | 58 (n = 5) |
| Isotype IgG3 | NT | 28 (n = 4) | NT | 43 (n = 4) |
| Isotype IgG3-Av | NT | 33 (n = 5) | NT | 40 (n = 4) |

Median survival is given in days.
NT = not tested.

There was one long-term survivor (more than 100 days) in the ch128.1Av-treated group and two in the ch128.1 group although no statistical significant difference in survival in this experiment between ch128.1Av and ch128.1 was found. Isotype controls were then tested to verify that targeting by the antibody was necessary for the anti-tumor effect. Again both ch128.1 and ch128.1Av exhibited significant protection compared to either buffer alone or their matched isotype controls. See FIG. 2A (Experiment #2). There were three long-term survivors in the group treated with ch128.1 in this experiment. In addition, ch128.1 prolonged survival compared to ch128.1Av (p<0.01). These studies demonstrate that despite the fact that ch128.1Av demonstrates stronger in vitro activity compared to ch128.1, a single dose of either ch128.1 or ch128.1Av resulted in dramatic anti-tumor effects in vivo against cells that are sensitive to both agents in vitro, especially to ch128.Av.

Figure 2B:
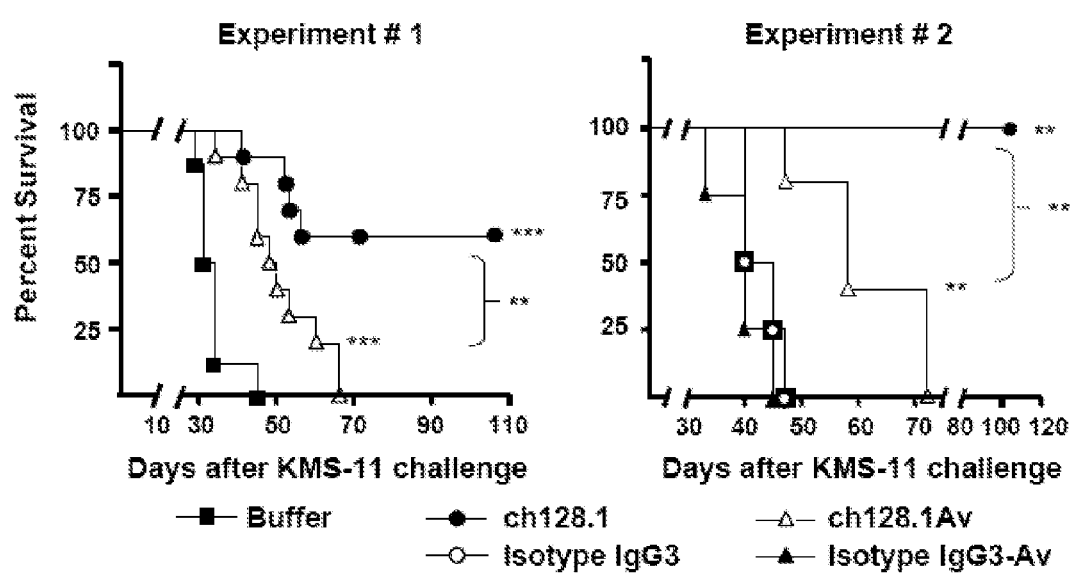
FIG. 2B are Kaplan-Meier plots showing the in vivo efficacy of ch128.1 and ch128.1Av against KMS-11. Female SCID-beige mice (8-12 weeks old) were radiated with 3 gray 24 hrs prior to the tumor challenge. The following day, mice were challenged with 5 million KMS-11 cells by intravenous injection via the tail vein. Two days later, mice were treated intravenously with buffer alone, ch128.1, or ch128.1Av (Experiment #1) or with buffer alone, ch128.1, ch128.1Av, isotype control of ch128.1 (isotype IgG3), or isotype control of ch128.1Av (isotype IgG3-Av), (Experiment #2). 125 µg of each treatment was used. Survival was recorded based on the time from tumor challenge to the development of hind-limb paralysis, when mice were euthanized. Kaplan-Meier plots were generated using GraphPad Prism (GraphPad Software, Inc., La Jolla, Calif.). * $p<0.05$,  $p<0.01$, * $p<0.001$, as determined by the Log Rank test. Animal numbers for each experiment are given in Table 1.

Using KMS-11 xenograft models, both ch128.1Av and ch128.1 significantly prolonged survival compared to buffer alone (FIG. 2B (Experiment #1), Table 1). There were several long-term survivors in the group treated with ch128.1, but none in the group treated with the fusion protein. Thus, ch128.1 showed significantly better protection compared to ch128.1Av (p<0.01). Again, isotype controls were tested and data from this second experiment showed results very similar to the first (FIG. 2B (Experiment #2), Table 1). Both ch128.1 and ch128.1Av significantly prolonged survival compared to controls, and ch128.1 demonstrated a stronger effect compared to ch128.1Av (FIG. 2B (Experiment #2), Table 1). Interestingly, all ch128.1-treated animals were long-term survivors and showed no evidence of disease. Surprisingly, these studies show that ch128.1 has strong in vivo anti-tumor activity, despite its total lack of in vitro activity against this cell line. In addition, in three out of the four in vivo experiments with the two cell lines, ch128.1 demonstrated statistically significant stronger in vivo anti-cancer activity compared to ch128.1Av.

These results evidence that ch128.1Av and ch128.1 may be used to treat human multiple myeloma and other hematopoietic malignancies. Therefore, the present invention provides methods for treating B-cell malignancies such as multiple myeloma and other hematopoietic malignancies in subjects, or other cancers in general, which comprise administering at least one unconjugated anti-TfR antibody.

It is noted that the in vivo efficacy of ch128.1 and ch128.1Av for treating a model of disseminated B-cell malignancy such as multiple myeloma is a dose that is much lower than what was used for A24 to treat a local (subcutaneous model) of a B-cell malignancy (lymphoma). See Lepelletier et al. (2007) Cancer Res 67(3):1145-1154, which is herein incorporated by reference.

As shown herein, ch128.1Av demonstrates stronger in vitro activity compared to ch128.1; however, a single low dose of ch128.1 resulted in significantly superior anti-tumor effects in vivo in ARH77 and KMS-11 models than ch128.1Av.

Therefore, the present invention provides methods for treating a cancer in a subject which comprises, consists essentially of, or consists of administering an unconjugated anti-TfR antibody as the sole or active therapeutic agents to the subject. In some embodiments, the method further comprises administering a secondary therapeutic agent to the subject. Secondary therapeutic agents include other anti-TfR antibodies which may be unconjugated or conjugated to another molecule, e.g. avidin. Other anti-TfR antibodies include the murine monoclonal anti-human TfR IgA antibody 42/6, the murine anti-human TfR IgG2b antibody A24, trastuzumab (anti-HER2/neu), elotuzumab (anti-CS1), mapatumumab (anti-TRAIL-R1), CNTO-328 (anti-IL-6), and milatuzumab (anti-CD74), rituximab (anti-CD20), and alemtuzumab (anti-CD52), and the like. See Brooks et al. (1995) Clin Cancer Res 1(11):1259-1265; Callens et al. (2010) J Exp Med 207(4):731-750; Wright J J (2010) Clin Cancer Res 16(16):4094-4104; Berkova et al. (2010) Expert Op Invest Drugs 19(1):141-149; Bello & Sotomayor (2007); Moura et al. (2004) Blood 103(5):1838-1845; Gennari et al. (2004) Clin Cancer Res 10(17):5650-5655; and Lozanski et al. (2004) Blood 103(9):3278-3281, which are herein incorporated by reference.

The unconjugated anti-TfR antibodies may or may not co-administered with one or more compounds such as additional anti-TfR antibodies including antibody-avidin fusion proteins which may or may not be linked to biotinylated drugs, toxins, genes encoding for toxins, chemotherapeutics, or cytokines such as interferon-γ, and the like. See Daniels et al. (2007) Mol Cancer Ther 6(11):2995-3008, which is herein incorporated by reference.

When one or more additional anti-TfR antibodies are administered as a secondary therapeutic agent, such additional anti-TfR antibodies, including antibody-avidin fusion proteins, may or may not be linked and/or co-administered with one or more compounds such as biotinylated drugs, toxins, genes encoding for toxins, chemotherapeutics, and cytokines such as interferon-γ, and the like.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A method of treating a B-cell malignancy in vivo in a subject or reducing the risk of the B-cell malignancy in vivo in the subject which comprises administering to the subject a therapeutically effective amount of at least one unconjugated anti-TfR antibody as the sole or primary therapeutic agent, wherein the unconjugated anti-TfR antibody comprises light and heavy chain variable regions of murine monoclonal 128.1, and wherein the unconjugated anti-TfR antibody is an IgG antibody.

2. The method of claim 1, wherein the unconjugated anti-TfR antibody is reactive with at least a portion of a human transferrin receptor.

3. The method of claim 1, wherein the unconjugated anti-TfR antibody is a chimeric human antibody, or a humanized antibody.

4. The method according to claim 2, wherein the human transferrin receptor is transferrin receptor protein 1 (TfR1).

5. The method of claim 1, wherein the unconjugated anti-TfR antibody further comprises human kappa light chain, and human gamma 3 heavy chain, and wherein the unconjugated anti-TfR antibody is specific for human transferrin receptor protein 1 (TfR1).

6. The method according to claim 1, wherein the unconjugated anti-TfR antibody is ch128.1 or 128.1.

7. The method of claim 1, wherein the unconjugated anti-TfR antibody is administered in the form of a pharmaceutical composition which comprises a pharmaceutically acceptable excipient.

8. The method of claim 1, wherein a secondary therapeutic agent is administered to the subject before, during, or after administration of the unconjugated anti-TfR antibody.

9. The method of claim 7, wherein the pharmaceutical composition further comprises a secondary therapeutic agent.

10. The method of claim 1, wherein the therapeutically effective amount of the unconjugated anti-TfR antibody is administered as a single dose or as multiple doses.

11. The method of claim 1, wherein the B-cell malignancy is multiple myeloma.

12. The method of claim 11, wherein the therapeutically effective amount of the unconjugated anti-TfR antibody is administered as a single dose or as multiple doses.

13. The method of claim 1, wherein the IgG antibody is an IgG1 or an IgG3 antibody.

* * * * *